United States Patent [19]

Shiozawa

[11] Patent Number: 5,207,823
[45] Date of Patent: May 4, 1993

[54] WOOD PRESERVATIVE COMPOSITION AND PROCESS FOR TREATING WOOD WITH THE SAME

[75] Inventor: Kazunobu Shiozawa, Osaka, Japan

[73] Assignee: Kabushiki Kaisha Koshii Preserving, Osaka, Japan

[21] Appl. No.: 678,383

[22] Filed: Apr. 1, 1991

[30] Foreign Application Priority Data

Apr. 3, 1990 [JP] Japan .................................. 2-89534
May 22, 1990 [JP] Japan ................................. 2-133501

[51] Int. Cl.$^5$ ............................................. C09D 5/14
[52] U.S. Cl. ............................... 106/18.13; 106/18.27; 106/18.3; 106/18.36
[58] Field of Search ................. 106/18.13, 18.27, 18.3, 106/18.36

[56] References Cited

U.S. PATENT DOCUMENTS

| | | | |
|---|---|---|---|
| 2,194,827 | 3/1940 | Gordon | 424/601 |
| 2,573,253 | 10/1951 | Farber | 106/18.12 |
| 2,769,730 | 11/1956 | Sakornbut | 106/18.3 |
| 5,071,478 | 12/1991 | Avelar | 106/18.13 |

FOREIGN PATENT DOCUMENTS

| | | |
|---|---|---|
| 1058353 | 7/1979 | Canada. |
| 0320786 | 12/1988 | European Pat. Off.. |
| 3447027 | 12/1984 | Fed. Rep. of Germany. |
| 2082912 | 8/1980 | United Kingdom. |

OTHER PUBLICATIONS

"Termite Resistance of Wood Treated with Copper (II) Compounds Derived From Tri-and Dialkylamine-boric Acid Complexes", by George C. Chen, Glenn R. Esenther, and Rober M. Rowell, Forest Products Journal, vol. 36, No. 5, May, 1986.

"Field Trials With Ammoniacal Copper Borate Wood Preservative", Forest Products Journal, vol. 33, No. 9, Sep., 1983.

"Ammoniacal Copper Borate: A New Treatment For Wood Preservation", Forest Products Journal, vol. 38, No. 2, Feb., 1978.

Chemical Abstracts, vol. 88, No. 20, May 15, 1978, p. 84 W. Kliegel: "BOR in Biologie, Medizin und Pharmazie", 1980, pp. 172-178.

Primary Examiner—Karl Group
Assistant Examiner—Anthony J. Green
Attorney, Agent, or Firm—Jordan and Hamburg

[57] ABSTRACT

A wood preservative composition includes a preservative component which is selected from the group consisting of copper borate and zinc borate, a volatile basic compound of, the formula $R_3N$, wherein R is one of a hydrogen atom and a lower alkyl group, and water. A process for preserving wood with the wood preservative composition includes impregnating wood with the the wood preservative composition and drying the impregnated wood to remove the volatile basic compound and water. The wood impregnated with the wood preservative composition is protected from wood-attacking organisms for a prolonged period of time without involving environmental pollution.

12 Claims, No Drawings

WOOD PRESERVATIVE COMPOSITION AND PROCESS FOR TREATING WOOD WITH THE SAME

BACKGROUND OF THE INVENTION

This invention relates to a wood preservative composition, process for treating wood with a wood preservative composition, and wood treated with a wood preservative composition.

As durable wood preservative composition conventionally, a water solution containing a metal compound and/or an inorganic compound has been used in a wide range for a long time. Such a solution is impregnated into wood to produce wood capable of keeping wood-attacking organisms from growing therein.

For example, the following compounds have been mainly used as preservative ingredients for wood preservative compositions; Copper compounds such as copper acetate, copper chromate; Chrome compounds such as potassium chromate, sodium dichromate; Mercury compounds such as mercury chloride; Arsenic compounds such as arsenious acid; Fluorine compounds such as sodium fluoride; and Boron compounds such as boric acid and borax. These compounds are mixed in a proper proportion and dissolved in water to produce a wood preservative solution.

In some cases, also, a fixing agent such as acetic acid or aqueous ammonia is added into the solution. When the solution containing such a fixing agent is impregnated into wood, chemical reactions between preservative ingredients, between a preservative ingredient and the fixing agent, and between a preservative ingredient and the wood take place, so that the preservative ingredient is fixed on the wood to ensure the wood preservative effect for a long period of time.

Especially, a combination of copper compound, chrome compound, and arsenic compound has been widely used as active preservative ingredients for a wood preservative composition. A solution containing these compounds has been called CCA preservative composition. Also, a combination of copper compound, chrome compound, and boric acid has been used as active preservative ingredients for a wood preservative composition. A solution containing these compounds has been called CCB preservative composition.

The CCA preservative composition and CCB preservative composition are comparatively cheap and have a long-time effectiveness. However, the arsenic compound is poisonous. Also, heavy metal compounds such as chrome and mercury have considerably high toxicity to warm-blooded animals.

Accordingly, severe attention has been necessary to pay to workers' health at the time of preparing such a preservative composition and treating wood with the preservative composition.

Also, in discarding unnecessary pieces of wood treated with such a preservative composition which inevitably are produced as by-product when the wood is cut into a desired form furniture made of wood treated with such a preservative composition, or building materials of wood treated with such a preservative composition, severe management has been required to prevent environmental pollution. Further, even if such scraps are burnt, toxic substances diffuse in the air or remain as ash for a long time and cause environmental problems.

Moreover, in addition to the problem of having high toxicity to warm-blooded animals, the CCB preservative composition has a problem that the boric acid is liable to be leached, which results in reduction of the preservative effectiveness.

To avoid the environmental pollution, use of organic metal compounds such as copper naphthenate, zinc naphthenate, or quaternary ammonium compounds has been proposed. However, these preservative ingredients have shorter-term effectiveness. Particularly, it has been impossible to employ these preservative ingredients for wood for building materials.

In view of the above-mentioned problems, a wood preservative composition has been desired which makes it possible to protect wood from wood attacking organisms for a prolonged period of time without involving environmental pollution. Also, eagerly have been desired a process for treating wood with a preservative composition capable of protecting wood from wood attacking organisms for a prolonged period of time without involving environmental pollution, and wood treated with a preservative composition capable of protecting wood from wood attacking organisms for a prolonged period of time without involving environmental pollution.

Accordingly, it is a first object of the present invention to provide a wood preservative composition which makes it possible to protect wood from wood attacking organisms for a prolonged period of time without involving environmental pollution.

Also, it is a second object of the present invention to provide a process for treating wood with a wood preservative composition capable of protecting wood from wood attacking organisms for a prolonged period of time without involving environmental pollution.

Further, it is a third object of the present invention to provide wood treated with a wood preservative composition capable of protecting wood from wood attacking organisms for a prolonged period of time without involving environmental pollution.

According to the present invention, a wood preservative composition comprises a preservative component which is selected from the group consisting of copper borate and zinc borate, a volatile basic compound of the formula $R_3N$, wherein R is one of a hydrogen atom and a lower alkyl group, and water.

According to the present invention, also, a process for preserving wood comprises the steps of impregnating wood with a wood preservative composition including a preservative component which is selected from the group consisting of copper borate and zinc borate, a volatile basic compound of the formula $R_3N$, wherein R is one of a hydrogen atom and a lower alkyl group, and water, and drying the impregnated wood to remove the volatile basic compound and water.

According to the present invention, further, a wood is produced by impregnating the wood with a wood preservative composition including a preservative component which is selected from the group consisting of copper borate and zinc borate, a volatile basic compound of the formula $R_3N$, wherein R is one of a hydrogen atom and a lower alkyl group and water, and drying the impregnated wood to remove the volatile basic compound and water.

The wood preservative composition of the present invention, which does not contain poisonous substances such as chrome compound and arsenic compound as in the CCA preservative composition, has the necessary anti-insect and anti-fungi effectiveness for a prolonged period of time without involving environmental pollution.

Also, the wood preservative composition of the present invention, which does not contain chrome compound and free boric acid as in the CCB preservative composition, has no toxicity to warm-blooded animals, and is not liable to be leached. Accordingly, the wood preservative composition can have the necessary anti-insect and anti-fungi effectiveness for a prolonged period of time.

Further, wood treated with the wood preservative composition of the present invention makes it possible to assure long use as safe wood materials for building, furniture, and the like.

These and other objects, features and advantages of the present invention will become more apparent upon a reading of the following detailed description.

DESCRIPTION OF THE PREFERRED EMBODIMENTS

In the present invention, the following starting materials are used.

1. COPPER TETRABORATE MONOBASIC—$Cu(OH)_2 \cdot CuB_4O_7$—

Copper Tetraborate, monobasic is prepared by a reaction of copper sulphate with borax. The reaction is seen to occur as shown in the following reaction formulas. Specifically, copper tetraborate is first produced as shown in FORMULA (1). The produced copper tetraborate is washed with water repeatedly to produce copper tetraborate, monobasic as shown in FORMULA (2).

$$CuSO_4 \cdot 5H_2O + Na_2B_4O_7 \cdot 10H_2O = CuB_4O_7 + Na_2SO_4 + 15H_2O \quad (1)$$

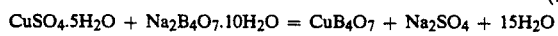
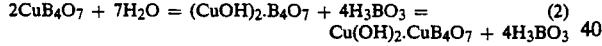

$$2CuB_4O_7 + 7H_2O = (CuOH)_2 \cdot B_4O_7 + 4H_3BO_3 = Cu(OH)_2 \cdot CuB_4O_7 + 4H_3BO_3 \quad (2)$$

As an example, 381.5 parts by weight (hereinafter called "parts") of a water solution containing 2 percent decahydrated borax $Na_2B_4O_7 \cdot 10 H_2O$ were added, under stirring, to 50 parts of a water solution containing 10 percent pentahydrated copper sulphate $CuSO_4 \cdot 5H_2O$ at room temperature, resulting in blue precipitation. The precipitate was filtered and washed with water repeatedly until unreacted borax was completely removed, and dried at 40° C. for 24–48 hours. Consequently, 2.69 grams of copper tetraborate, monobasic were obtained.

2. COPPER TETRABORATE DIBASIC—$2Cu(OH)_2 \cdot CuB_4O_7$—

Copper Tetraborate,dibasic is prepared by mixing a solution containing a high concentration of copper sulphate and a solution containing a high concentration of borax at a remarkably high temperature, e.g., 50° C. Specifically, immediately after copper tetraborate is produced as shown in FORMULA (1), as shown in FORMULA (3), a hydrolysis occurs to produce copper tetraborate,dibasic.

$$3CuB_4O_7 + 14H_2O = (CuOH)_3 \cdot B_4O_7 \cdot (OH) + \quad (3)$$

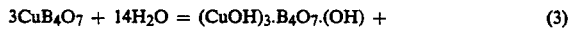

$$2H_2BO_4O_7 + 10H_2O = \{2Cu(OH)_2\} \cdot CuB_4O_7 + 8H_3BO_3$$

For example, 763 parts of a water solution containing 10 percent decahydrated borax $Na_2B_4O_7 \cdot 10 H_2O$ were added, under stirring, to 125 parts of a water solution containing 40 percent pentahydrated copper sulphate $CuSO_4 \cdot 5H_2O$ at 50° C. The solution was kept at 50° C. for 1 hour, and then kept at 20°–30° C. for one night, consequently resulting in a precipitate. The precipitation was filtered and washed with water repeatedly until unreacted borax was completely removed and dried at 40° C. Consequently, 26.81 grams of copper tetraborate,dibasic were obtained.

3. COPPER TETRABORATE TRIBASIC—$3Cu(OH)_2 \cdot CuB_4O_7$—

Copper tetraborate,tribasic is prepared by mixing a solution containing a high concentration of copper sulphate and a solution containing a high concentration of borax at a remarkably high temperature, e.g., 60° C. while adding a greater amount of water and maintaining a ratio of one mole copper sulphate to one mole borax. Specifically, after copper tetraborate is produced as shown in FORMULA (1), water washing is executed repeatedly to produce copper tetraborate,tribasic as shown in FORMULA (4).

$$4CuB_4O_7 + 21H_2O = (CuOH)_4B_4O_7 \cdot (OH)_2 + \quad (4)$$

$$3H_2B_4O_7 + 15H_2O = \{3Cu(OH)_2\} \cdot CuB_4O_7 + 12H_3BO_3$$

For example, 12.5 parts of a water solution containing 40 percent pentahydrated copper sulphate $CuSO_4 \cdot 5H_2O$ and 75 parts of water solution containing 10.2 percent decahydrated borax $Na_2B_4O_7 \cdot 10 H_2O$ were mixed while maintaining a ratio of 1 to 6. i.e., a ratio of one mole to one mole. at 60° C. 100 parts of water were added into the solution at 60° C. which was kept at 60° C. for 1 hour, and then kept at 20°–30° C. for one night, consequently resulting in a precipitation. The precipitate was filtered and washed with water repeatedly until unreacted borax was completely removed, and dried at 60° C. for 48 hours. Consequently, 2.43 grams of copper tetraborate,tribasic were obtained.

It has been known that copper or copper compounds are toxic to wood-attacking fungi, and boric acid is toxic to wood-attacking insects, such as termite. Accordingly, it will be seen that the above-mentioned three copper borates are toxic to both wood-attacking fungi and wood-attacking insects because of having a copper component and a boric acid component.

Also, the above-mentioned three copper borates are insoluble in water. In particular, it is unlikely that the three copper borates decompose to release boric acid even when the above-mentioned three copper borates are dissolved in water. Accordingly, the three copper borates are rarely leached, and thus can maintain the wood preservative effect for a prolonged period of time.

4. ZINC TETRABORATE DIBASIC—$2Zn(OH)_2 \cdot ZnB_4O_7$—

Zinc tetraborate,dibasic is prepared by a reaction of zinc chloride with borax. The reaction is seen to occur as shown in the following reaction formulas. Specifically, zinc tetraborate is first produced as shown in FORMULA (5). The produced copper tetraborate is immediately hydrolysed to produce zinc tetraborate, dibasic as shown in FORMULA (6).

$$ZnCl_2 + Na_2B_4O_7 \cdot 10H_2O = ZnB_4O_7 + 2NaCl + 10H_2O \quad (5)$$

$$6ZnB_4O_7 + 28H_2O = 2\{(ZnOH)_3 \cdot B_4O_7(OH)\} + \quad (6)$$
$$16H_3BO_3 = 2[\{Zn(OH)_2\} \cdot ZnB_4O_7] + 16H_3BO_3$$

As an example, 381.5 parts of a water solution containing 2 percent decahydrated borax $Na_2B_4O_7 \cdot 10H_2O$ were added, under stirring, to 27.3 parts of a water solution containing 10 percent zinc chloride $ZnCl_2$ at room temperature, resulting in a white-colored precipitation. The precipitate was filtered and washed with water repeatedly until unreacted borax was completely removed, and dried at 40° C. for 24 hours or more until the reduction of weight of the precipitate diminished. Consequently, 2.90 grams of zinc tetraborate,dibasic were obtained.

When dissolved in water in the presence of a volatile basic compound, zinc tetraborate,dibasic decomposes to produce zinc tetraborate,pentabasic as shown in FORMULA (7).

$$2[\{2Zn(OH)_2\} \cdot ZnB_4O_7] + 7H_2O = (ZnOH)_6 \cdot B_4O_7(OH)_4 + \quad (7)$$
$$4H_3BO_3 = \{5Zn(OH)_2\} \cdot ZnB_4O_7 + 4H_3BO_3$$

The above-mentioned zinc tetraborate dibasics are called Zinc tetraborate tribasic, monohydroxide and represented by $(ZnOH)_3 \cdot B_4O_7(OH)$.

5. TETRA ZINCHYDROXIDE TRI(TETRABORIC ACID) SALT—$4Zn(OH)_2 \cdot 3H_2B_4O_7$—

This compound is produced and sold by Tomita Seiyaku Kabushiki Kaisha, a Japanese chemical company, under a brand name of "ZINC BORATE 2335", and thus easily available.

This zinc borate is dissolved in water in the presence of a volatile basic compound to produce tetra zinchydroxide di(tetraboric acid) salt as shown in FORMULA (8).

$$4Zn(OH)_2 \cdot 3H_2B_4O_7 + 5H_2O = 4Zn(OH)_2 \cdot 2H_2B_4O_7 + 4H_3BO_3 \quad (8)$$

6 ZINC HYDROXIDE DIMETABORIC ACID SALT—$Zn(OH)_2 \cdot (2HBO_2)$ or $ZnO \cdot B_2O_3 \cdot 2H_2O$—

This compound is produced and sold by Tomita Seiyaku Kabushiki Kaisha under a brand name of "Zinc Borate 101", and thus easily available.

When this zinc borate is dissolved in water in the presence of a volatile basic compound, a hydrolysis occurs to produce zinchydroxide,monomeraboric acid salt as shown in FORMULA (9).

$$Zn(OH)_2 \cdot 2HBO_2 + H_2O = Zn(OH)_2 \cdot HBO_2 + H_3BO_3 \quad (9)$$

As mentioned earlier, boric acid is toxic to wood-attacking insects. Also, zinc or zinc compounds are toxic to wood-attacking fungi. Accordingly, it will be seen that the above-mentioned zinc borates are toxic to both wood-attacking fungi and wood-attacking insects.

Also, when zinc tetraborate,dibasic, tetra zinchydroxide tri(tetraboric acid) salt, and zinc hydroxide,-dimetaboric acid salt are dissolved in water in the presence of a volatile basic compound:

1) the zinc tetraborate,dibasic causes zinc tetraborate,pentabasic;
2) the tetra zinchydroxide,tri(tetraboric acid) salt causes tetra zinchydroxide di(tetraboric acid) salt and
3) the zinchydroxide,dimetaboric acid salt causes zinc hydroxide,monometaboric acid salt.

In these reactions, a negligibly small quantity of boric acid is released, and then leached. However, an almost quantity of boric acid remains, and is thus unlikely to be leached. Accordingly, the preservative effectiveness is maintained for a prolonged time.

A reason why an almost quantity of boric acid is not leached when employing both copper borate and zinc borate can be explained as follows. Copper borate and zinc borate impregnated into wood may have the following hydrolysis balances:

$$\text{Copper borate} \rightleftharpoons \text{Boric acid} + \text{Copper borate basic} \quad (9)$$

$$\text{Zinc borate} \rightleftharpoons \text{Boric acid} + \text{Zinc borate basic} \quad (10)$$

In one of the above opposite reactions, boric acid is produced. Accordingly, the concentration of boric acid progressively increases and exceeds a threshold concentration, which consequently causes the opposite reaction and prevents the hydrolysis.

When dissolving only copper borate in water to prepare a wood preservative composition, appropriate parts of copper borate may be replaced with other inexpensive copper compounds to reduce the preparation costs. As inexpensive copper compounds can be cited copper acetate, copper hydroxide, or copper chloride. Also, copper borate has slightly lower toxicity than zinc borate against wood attacking insects. Accordingly, an appropriate amount of zinc borate may be added into a wood preservative composition containing copper borate to increase the insect toxicity of the wood preservative composition.

When dissolving only zinc borate in water to prepare a wood preservative composition, appropriate parts of zinc borate may be replaced with other inexpensive zinc compounds to reduce the preparation costs. As inexpensive zinc compounds can be cited zinc acetate, zinc hydroxide, or zinc chloride. Also, zinc borate has slightly lower toxicity than copper borate against wood-attacking fungi. Accordingly, an appropriate amount of copper borate may be added into a wood preservative composition containing zinc borate to increase the fungus toxicity of the wood preservative composition.

Also, it will be seen that copper borate and zinc borate are dissolved in water in an appropriate proportion to produce an optimum preservative composition which has both high insect toxicity and high fungus toxicity for a prolonged period of time.

In the present invention, the following volatile basic compounds may be used: primary, secondary and tertiary amines having a boiling point of 100 or less Centigrade degrees, such as ammonia (in the form of aqueous ammonia), monomethylamine, dimethylamine, trimethylamine, monopropylamine, dipropylamine, tripropylamine, and monopentylamine and the like.

Also, it is preferable to add ammonium compounds, such as ammonium chloride, ammonium carbonate, as a dissolving agent to increase the dissolving rate of copper borate and zinc borate, and assure a stabilized solution.

Further, it is preferable to add the following penetrating agents: aliphatic dihydric alcohol such as ethylene glycol, propylene glycol, and water soluble alkyl ether of the aliphatic dihydric alcohol, water soluble alkyl ester of the aliphatic dihydric alcohol, and various other known kinds of surfactant.

Furthermore, it is preferable to add aromatic agents such as perfume, and coloring agents such as dyestuff.

In preparation Of a wood preservative composition using only copper borate as preservative ingredient, 0.1-5 parts of copper borate are added with respect to 100 parts of the wood preservative composition. The greater the quantity of copper borate added, the higher the anti-insect and anti-fungi effect is because more copper borate is fixed on wood. However, in the case of more than 5 parts, copper borate is difficult to dissolve in the composition. Also, wood is highly colored. In the case of less than 0.1 parts, a desired anti-insect and anti-fungi effect cannot be obtained. Furthermore, it is preferable to use 0.5-2 parts of copper borate with respect to 100 parts of the wood preservative composition.

When adding a volatile basic compound, 80-160 parts of volatile basic compound is added with respect to 100 parts of copper borate. In the case of less than 80 parts, the solubility of copper borate is insufficient. In the case of more than 160 parts, a stronger odor occurs. It is preferable to use 80-100 parts of volatile basic compound with respect to 100 parts of copper borate.

When adding an auxiliary dissolving agent such as ammonium chloride, a preferable proportion is 10-30 parts of auxiliary dissolving agent to 100 parts of copper borate.

In preparation of a wood preservative composition using only zinc borate as preservative ingredient, 0.1-10 parts of zinc borate are added with respect to 100 parts of the wood preservative composition. The greater the quantity of zinc borate added, the higher the anti-insect and anti-fungi effect is because of more quantity of zinc borate is fixed on wood. However, in the case of more than 10 parts, zinc borate is difficult to dissolve in the composition. In the case of less than 0.1 parts, a desired anti-insect and anti-fungi effect cannot be obtained. It is further preferable to use 0.5-2 parts of zinc borate with respect to 100 parts of the wood preservative composition.

When adding a volatile basic compound, 75-160 parts of volatile basic compound are added with respect to 100 parts of zinc borate. In the case of less than 75 parts, the solubility of zinc borate is insufficient. In the case of more than 160 parts, a stronger odor occurs. It is preferable to use 75-100 parts of volatile basic compound with respect to 100 parts of zinc borate.

When adding an auxiliary dissolving agent such as ammonium chloride, a preferable proportion is 10-100 parts of auxiliary dissolving agent to 100 parts of zinc borate.

In preparation of a wood preservative composition using both copper borate and zinc borate as preservative ingredient, 0.1-10 parts of mixture of copper borate and zinc borate are added with respect to 100 parts of the wood preservative composition. Also, a volatile basic compound and auxiliary dissolving agent are preferably added. The proportions of volatile basic compound and auxiliary dissolving agent may be determined in accordance with the respective quantities of copper borate and zinc borate.

Further, appropriate quantities of penetrating agent, aromatic agent, and coloring agent may be added depending on the occasion.

The preparation of the wood preservative compositions of the present invention will now be explained.

In preparation of a wood preservative composition containing copper borate as preservative ingredient, firstly, an aqueous ammonia or other volatile basic compound is dissolved in water to prepare a water solution. Secondly, a proper quantity of copper borate is added to the water solution at room temperature, and then stirred to completely dissolve it in the water solution. If required, in addition to copper borate, appropriate quantities of another copper compound, zinc compound, and additives are added and stirred in the water solution.

As another preparation, a first water solution which contains copper borate, and a second water solution which contains another copper compound, zinc compound, and additives are separately prepared. Thereafter, the first water solution and the second water solution are mixed to prepare a wood preservative composition containing copper borate as preservative ingredient.

In preparation of a wood preservative composition containing zinc borate as wood preservative ingredient, firstly, zinc borate and a small quantity of water are mixed at room temperature to prepare a paste or slurry. Secondly, an appropriate quantity of aqueous ammonia or other volatile basic compound is added to the paste or slurry, and stirred to prepare a solution. Finally, a necessary quantity of water is added to the solution to prepare the wood preservative composition containing a desired concentration of zinc borate. Also, if required, in the first step, appropriate quantities of another zinc compound, copper compound, and additives are added in addition to zinc borate to prepare a mixture in the form of a paste or slurry.

As another preparation, a first water solution which contains zinc borate, and a second water solution which contains another zinc compound, copper compound, and additives are separately prepared. Thereafter, the first water solution and the second water solution are mixed to prepare a wood preservative composition containing zinc borate as preservative ingredient.

In preparation of a wood preservative composition containing copper borate and zinc borate as preservative ingredients, firstly, copper borate, zinc borate and a small quantity of water are mixed at room temperature to prepare a paste or slurry. Secondly, an appropriate quantity of aqueous ammonia or other volatile basic compound is added to the paste or slurry, and stirred to prepare a solution. Finally, a necessary quantity of water is added to the solution to prepare a wood preservative composition containing copper borate and zinc borate as preservative ingredients. Also, if required, in the first step, appropriate quantities of another copper compound, zinc compound, and additives are added.

As another preparation, a first water solution which contains copper borate, and a second water solution which contains zinc borate are separately prepared. Thereafter, the first water solution and the second water solution are mixed to prepare a wood preservative composition containing copper borate and zinc borate as preservative ingredients.

The above-prepared solution is impregnated into wood in the following way. A closed chamber is filled with the preservative impregnating solution. Wood is placed in the chamber. The pressure in the chamber is reduced to a pressure of 600–700 mm Hg so that air in the wood is evacuated. Thereafter, the pressure in the chamber is restored to a normal pressure so that the wood preservative solution is impregnated into the wood.

Also, the wood preservative solution may be impregnated into wood at a high pressure of 5–20 kg/cm², or at usual temperature and pressure, by means of known impregnating equipment.

The above-impregnated wood is naturally dried by placing it in the air for several days, or forcibly dried by heating it at a temperature of 50°–60° C. so as to remove the volatile basic compound and water from the impregnated wood. Consequently wood fixed with wood preservative is obtained.

The following examples and test examples illustrate the present invention in greater detail.

EXAMPLE 1

| | |
|---|---|
| Copper tetraborate, monobasic | 1.140 parts |
| and Ammonium chloride | 0.30 parts |
| were entirely mixed in the form of a powder | |
| Aqueous ammonia (25 percent) | 3.80 parts |
| were added to the mixture, and stirred to partially dissolve the compounds. | |
| Water | 24.76 parts |
| were added to the composition, and stirred to completely dissolve the compounds. | |
| Water | 70.00 parts |
| were further added and stirred. | |

Consequently, a preservative composition or impregnating solution was obtained which was homogeneous and blue in color.

EXAMPLE 2

| | |
|---|---|
| Copper tetraborate, monobasic | 0.770 parts |
| Trimethylamine solution (30 percent) | 10.09 parts |
| Ammonium chloride | 2.02 parts |
| and Water | 87.12 parts | were mixed under stirring in steps similar to EXAMPLE 1. Consequently, a preservative composition was obtained.

EXAMPLE 3

A first solution

| | |
|---|---|
| Copper tetraborate, monobasic | 0.380 parts |
| Aqueous ammonia (25 percent) | 1.26 parts |
| Ammonium chloride | 0.10 parts |
| and Water | 92.06 parts | were mixed under stirring in steps similar to EXAMPLE 1. Consequently, a first solution was obtained which was homogeneous and blue in color.

A second solution

| | |
|---|---|
| Zinc chloride | 10.4 parts |
| were dissolved in | |
| Water | 31.6 parts |
| to produce a semitransparent solution. | |
| Aqueous ammonia (25 percent) | 21.0 parts | were immediately added to the solution, and stirred until a transparent solution was obtained.

| | |
|---|---|
| Water | 37.0 parts |
| were further added and stirred. Consequently, | |
| A transparent solution | 100.0 parts |
| were obtained in the state of a semi-transparent solution. This transparent solution was the second solution. | |
| The first solution | 93.8 parts |
| and the second solution | 6.2 parts |
| were mixed under stirring. Consequently, a preservative composition was obtained which was homogeneous and blue in color. | |

EXAMPLE 4

| | |
|---|---|
| Copper tetraborate, monobasic | 0.380 parts |
| Aqueous ammonia (25 percent) | 2.92 parts |
| and Water | 96.70 parts | were mixed under stirring in steps similar to Example 1. Consequently, a preservative composition was obtained which was homogeneous and blue in color. This example required slightly longer time to obtain the homogeneous blue solution than EXAMPLE 1.

EXAMPLE 5

| | |
|---|---|
| Copper tetraborate, dibasic | 0.334 parts |
| Ammonium bicarbonate | 0.62 parts |
| Aqueous ammonia (25 percent) | 0.58 parts |
| and Water | 98.466 parts | were mixed under stirring in steps similar to EXAMPLE 1. Consequently, a preservative composition was obtained.

EXAMPLE 6

| | |
|---|---|
| Copper tetraborate, tribasic | 0.310 parts |
| Aqueous ammonia (25 percent) | 0.54 parts |
| Ammonium bicarbonate | 0.55 parts |
| and Water | 98.60 parts | were mixed under stirring in steps similar to EXAMPLE 1. Consequently, a preservative composition was obtained.

EXAMPLE 7

| | |
|---|---|
| Zinc tetraborate, dibasic | 1.315 parts |
| and Ammonium chloride | 2.05 parts |
| was entirely mixed in the form of a powder. | |
| Aqueous ammonia (25 percent) | 6.13 parts |
| were added to the mixture, and kneaded to obtain a homogeneous composition. | |
| Water | 20.00 parts |
| were added to the composition, and stirred to completely dissolve the compounds. | |
| Water | 70.505 parts |
| were further added and stirred, so that a preservative composition was obtained which had an appropriate concentration. | |

EXAMPLE 8

| | |
|---|---|
| Tetra zinchydroxide, tri(tetraboric acid) salt (in the trademark of ZINC BORATE 2335) | 1.023 parts |
| Aqueous ammonia (25 percent) | 3.07 parts |
| Ammonium chloride | 1.02 parts |
| and Water | 94.887 parts | were mixed in steps similar to EXAMPLE 7. Consequently, a preservative composition was obtained.

EXAMPLE 9

| | |
|---|---|
| Tetra zinchydroxide, tri(tetraboric acid) salt (in the trademark of ZINC BORATE 2335) | 1.023 parts |
| Triethylamine solution (30 percent) | 15.21 parts |
| Ammonium chloride | 2.41 parts |
| and Water | 81.357 parts | were mixed in steps similar to EXAMPLE 7. Consequently, a preservative composition was obtained.

EXAMPLE 10

| | |
|---|---|
| Tetra zinchydroxide, tri(tetraboric acid) salt (in the trademark of ZINC BORATE 2335) | 1.030 parts |
| Pentahydrated copper sulphate | 0.605 parts |
| Ammonium chloride | 1.03 parts |
| Aqueous ammonia (25 percent) | 4.09 parts |
| and Water | 93.245 parts | were mixed in steps similar to EXAMPLE 7. Consequently, a preservative composition was obtained.

EXAMPLE 11

| | |
|---|---|
| Tetra zinchydroxide, tri(tetraboric acid) salt (in the trademark of ZINC BORATE 2335) | 1.030 parts |
| Aqueous ammonia (25 percent) | 0.75 parts |
| and Water | 98.22 parts | were stirred at room temperature for 27 hours, and mixed in steps similar to EXAMPLE 7. Consequently, a preservative composition was obtained.

Also, when 1.00 part of water was replaced with ammonium chloride, another preservative composition was obtained by stirring the solution for 2 hours. Accordingly, it will be seen that ammonium compounds such as ammonium chloride are effective to increase the dissolving rate.

EXAMPLE 12

| | |
|---|---|
| Zinc hydroxide, dimetaboric acid salt (in the trademark of ZINC BORATE 101) | 0.890 parts |
| Aqueous ammonia (25 percent) | 4.88 parts |
| Ammonium chloride | 0.09 parts |
| and Water | 94.14 parts | were mixed in steps similar to EXAMPLE 7. Consequently, a preservative composition was obtained.

EXAMPLE 13

| | |
|---|---|
| Copper tetraborate, monobasic | 0.383 parts |
| Zinc tetraborate, dibasic salt | 0.659 parts |
| Aqueous ammonia (25 percent) | 5.98 parts |
| Ammonium chloride | 1.11 parts |
| and Water | 91.868 parts | were mixed in steps similar to EXAMPLE 7. Consequently, a preservative composition was obtained.

EXAMPLE 14

A first solution

| | |
|---|---|
| Copper tetraborate monobasic | 0.192 parts |
| Aqueous ammonia (25 percent) | 1.46 parts |
| Ammonium chloride | 0.04 parts |
| and Water | 48.308 parts | were mixed in steps similar to EXAMPLE 1. Consequently, a first solution was prepared which was homogeneous and blue in color.

A second solution

| | |
|---|---|
| Tetra zinchydroxide, tri(tetraboric acid) salt (in the trademark of ZINC BORATE 2335) | 0.512 parts |
| Aqueous ammonia (25 percent) | 1.53 parts |
| Ammonium chloride | 0.51 parts |
| and Water | 47.448 parts | were mixed in steps similar to EXAMPLE 7. Consequently, a second solution was prepared which was colorless and homogeneous.

Thereafter, the first solution and the second solution were mixed, so that a preservative composition was obtained.

EXAMPLE 15

A first solution

| | |
|---|---|
| Copper tetraborate monobasic | 0.383 parts |
| Aqueous ammonia (25 percent) | 2.91 parts |
| Ammonium chloride | 0.08 parts |
| and Water | 46.627 parts | were mixed in steps similar to EXAMPLE 1. Consequently, a first solution was prepared which was homogeneous and blue in color.

A second solution

| | |
|---|---|
| Tetra zinchydroxide, tri(tetraboric acid) salt (in the trademark of ZINC BORATE 2335) | 1.535 parts |
| Aqueous ammonia (25 percent) | 4.61 parts |
| Ammonium chloride | 1.54 parts |
| and Water | 42.315 parts | were mixed in steps similar to EXAMPLE 7. Consequently, a second solution was prepared which was colorless and homogeneous.

Thereafter, the first solution and the second solution were mixed, so that a preservative composition was obtained.

EXAMPLE 16

A first solution

| Copper tetraborate monobasic | 0.767 parts |
|---|---|
| Aqueous ammonia (25 percent) | 5.82 parts |
| Ammonium chloride | 0.16 parts |
| and Water | 43.253 parts | were mixed in steps similar to EXAMPLE 1. Consequently, a first solution was prepared which was homogeneous and blue in color.

A second solution

| Tetra zinchydroxide, tri(tetraboric acid) salt (in the trademark of ZINC BORATE 2335) | 2.043 parts |
|---|---|
| Aqueous ammonia (25 percent) | 6.13 parts |
| Ammonium chloride | 2.04 parts |
| and Water | 39.787 parts | were mixed in steps similar to EXAMPLE 7. Consequently, a second solution was prepared which was colorless and homogeneous.

Thereafter, the first solution and the second solution were mixed, so that a preservative composition was obtained.

EXAMPLE 17

A first solution

| Copper tetraborate monobasic | 0.383 parts |
|---|---|
| Aqueous ammonia (25 percent) | 2.91 parts |
| and Water | 46.707 parts | were mixed in steps similar to EXAMPLE 1. Consequently, a first solution was prepared which was homogeneous and blue in color.

A second solution

| Tetra zinchydroxide, tri(tetraboric acid) salt (in the trademark of ZINC BORATE 2335) | 1.030 parts |
|---|---|
| Aqueous ammonia (25 percent) | 3.09 parts |
| and Water | 45.88 parts | were mixed in steps similar to EXAMPLE 7. Consequently, a second solution was prepared which was colorless and homogeneous.

Thereafter, the first solution and the second solution were mixed, so that a preservative composition was obtained.

EXAMPLE 18

A first solution

| Copper tetraborate monobasic | 0.192 parts |
|---|---|
| Aqueous ammonia (25 percent) | 0.64 parts |
| Ammonium chloride | 0.05 parts |
| and Water | 49.118 parts | were mixed in steps similar to EXAMPLE 1. Consequently, a first solution was prepared which was homogeneous and blue in color.

A second solution

| Zinc hydroxide, dimetaboric acid salt (in the trademark of ZINC BORATE 101) | 0.440 parts |
|---|---|
| Aqueous ammonia (25 percent) | 2.41 parts |
| Ammonium chloride | 0.04 parts |
| and Water | 47.11 parts | were mixed in steps similar to EXAMPLE 7. Consequently, a second solution was prepared which was colorless and homogeneous.

Thereafter, the first solution and the second solution were mixed, so that a preservative composition was obtained.

EXAMPLE 19

A first solution

| Copper tetraborate monobasic | 0.383 parts |
|---|---|
| Aqueous ammonia (25 percent) | 1.28 parts |
| Ammonium chloride | 0.10 parts |
| and Water | 48.237 parts | were mixed in steps similar to EXAMPLE 1. Consequently, a first solution was prepared which was homogeneous and blue in color.

A second solution

| Zinc hydroxide, dimetaboric acid salt (in the trademark of ZINC BORATE 101) | 0.890 parts |
|---|---|
| Aqueous ammonia (25 percent) | 4.88 parts |
| Ammonium chloride | 0.09 parts |
| and Water | 44.14 parts | were mixed in steps similar to EXAMPLE 7. Consequently, a second solution was prepared which was colorless and homogeneous.

Thereafter, the first solution and the second solution were mixed, so that a preservative composition was obtained.

EXAMPLE 20

A first solution

| Copper tetraborate dibasic | 0.167 parts |
|---|---|
| Aqueous ammonia (25 percent) | 0.29 parts |
| Ammonium bicarbonate | 0.31 parts |
| and Water | 49.233 parts | were mixed in steps similar to EXAMPLE 1. Consequently, a first solution was prepared which was homogeneous and blue in color.

A second solution

| Tetra zinchydroxide, tri(tetraboric acid) salt (in the trademark of ZINC BORATE 2335) | 0.511 parts |
|---|---|
| Aqueous ammonia (25 percent) | 0.99 parts |
| Ammonium chloride | 0.17 parts |
| Ethylenediamine | 0.03 parts |
| and Water | 48.299 parts | were mixed in steps similar to EXAMPLE 7. Consequently, a second solution was prepared which was and homogeneous.

Thereafter, the first solution and the second solution were mixed, so that a preservative composition was obtained.

EXAMPLE 21

A first solution

| | | |
|---|---|---|
| Copper tetraborate dibasic | 0.167 | parts |
| Aqueous ammonia (25 percent) | 0.29 | parts |
| Ammonium bicarbonate | 0.31 | parts |
| and Water | 49.233 | parts | were mixed in steps similar to EXAMPLE 1. Consequently, a first solution was prepared which was homogeneous and blue in color.

A second solution

| | | |
|---|---|---|
| Tetra zinchydroxide, tri(tetraboric acid) salt (in the trademark of ZINC BORATE 2335) | 1.023 | parts |
| Aqueous ammonia (25 percent) | 1.98 | parts |
| Ammonium chloride | 0.34 | parts |
| Ethylenediamine | 0.07 | parts |
| and Water | 46.587 | parts | were mixed in steps similar to EXAMPLE 7. Consequently, a second solution was prepared which was colorless and homogeneous.

Thereafter, the first solution and the second solution were mixed, so that a preservative composition was obtained.

EXAMPLE 22

A first solution

| | | |
|---|---|---|
| Copper tetraborate tribasic | 0.154 | parts |
| Aqueous ammonia (25 percent) | 0.27 | parts |
| Ammonium bicarbonate | 0.28 | parts |
| and Water | 49.296 | parts | were mixed in steps similar to EXAMPLE 1. Consequently, a first solution was prepared which was homogeneous and blue in color.

A second solution

| | | |
|---|---|---|
| Tetra zinchydroxide, tri(tetraboric acid) salt (in the trademark of ZINC BORATE 2335) | 0.510 | parts |
| Aqueous ammonia (25 percent) | 0.99 | parts |
| Ammonium chloride | 0.17 | parts |
| Ethylenediamine | 0.03 | parts |
| and Water | 48.30 | parts | were mixed in steps similar to EXAMPLE 7. Consequently, a second solution was prepared which was colorless and homogeneous.

Thereafter, the first solution and the second solution were mixed, so that a preservative composition was obtained.

EXAMPLE 23

A first solution

| | | |
|---|---|---|
| Copper tetraborate tribasic | 0.077 | parts |
| Aqueous ammonia (25 percent) | 0.19 | parts |
| Ammonium bicarbonate | 0.14 | parts |
| and Water | 49.593 | parts | were mixed in steps similar to EXAMPLE 1. Consequently, a first solution was prepared which was homogeneous and blue in color.

A second solution

| | | |
|---|---|---|
| Tetra zinchydroxide, tri(tetraboric acid) salt (in the trademark of ZINC BORATE 2335) | 0.770 | parts |
| Aqueous ammonia (25 percent) | 1.49 | parts |
| Ammonium chloride | 0.26 | parts |
| Ethylenediamine | 0.05 | parts |
| and Water | 47.43 | parts | were mixed in steps similar to EXAMPLE 7. Consequently, a second solution was prepared which was colorless and homogeneous.

Thereafter, the first solution and the second solution were mixed, so that a preservative composition was obtained.

Wood was treated with the wood preservative compositions obtained in EXAMPLES 1 to 23 as follows.

The obtained wood preservative composition was filled in a water-tight closed chamber. A sapwood piece of Japanese red pine of $1 \times 2 \times 5$ cm in size was placed in the wood preservative composition. The pressure in the chamber was reduced to 700 mm Hg. The sapwood piece was impregnated with the wood preservative composition by holding it in the wood preservative composition for 10–20 minutes.

The impregnated sapwood piece was dried by placing it in air at room temperature for 1–2 days, and then dried by heating it at a temperature of 60° C. for 48 hours so as to completely remove the volatile basic compound and water. Consequently, wood fixed with the wood preservative was obtained.

The amount of wood preservative composition with respect to the sapwood piece, the respective absorption amounts of copper borate, zinc borate, copper, zinc, and boric acid equivalent to boron of the active ingredient, and the respective leaching rates of copper, zinc, boric acid equivalent to boron of the active ingredient, are shown in TABLES 1-1, 1-2. It could be seen in TABLES 1-1, and 1-2 that each of the wood preservative compositions of EXAMPLES 1-23 provided quite good fixing of wood preservatives. It should be noted that in TABLE 1-1, Z/B denotes zinc borate, C/B denotes copper borate, Fixed B denotes fixed boric acid, and Free B denotes free boric acid. Also, it should be noted that in EXAMPLE 3, zinc chloride was absorbed in place of zinc borate, and in EXAMPLE 10, copper sulphate was absorbed in place of copper borate.

The leaching rate of wood preservative compositions Of EXAMPLES 1-23 is calculated as follows. Three treated wood pieces were placed in a 500ml beaker, and 400 ml pure water were poured into the beaker and stirred at room temperature for 48 hours to leach preservative ingredients. The amount of each leached-out preservative ingredient was measured, and the leaching rate (LR) of the preservative ingredient was calculated in accordance with the following equation:

$$LR = A/B \times 100$$

wherein A denotes the amount of preservative ingredient leached out in the pure water, and B denotes the amount of preservative ingredient absorbed in the wood piece.

The anti-fungi effectivenesses of wood preservative compositions of EXAMPLES 1-23 was tested. The test was made based on JIS A9302, "TESTING METHOD OF ANTI-FUNGI EFFECTIVENESS OF WOOD PRESERVATIVE COMPOSITION". Specifically, sterilized sea sand is placed in a wide-mouthed bottle. A culture solution including glucose peptone and an extract of malt are poured into the bottle. The following fungi are used for the test:

Coriolellus Palustris (BERK, et CORT) MURR Linshi 0507; and

Coriolus Versicolor (Lex FR) QUEL Linshi 1030.

The fungi were cultured in the bottle at a temperature of 26° C. under 70% RH for 10-15 days. A sapwood of Japanese cedar of $2 \times 2 \times 1$ cm in size so treated is placed in the bottle as a test piece and left at a temperature of 26° C. under 70% RH for 90 days. The weights of the test piece before and after the test are measured. The average weight reduction rates and anti-fungi effectiveness were calculated from the obtained measurements. TABLES 2-1 and 2-2 show results of the wood preservative compositions of EXAMPLES 1-23 in accordance with the above-mentioned test method.

The anti-fungi effectiveness (AFE) was calculated on the basis of the following equation:

$$AFE = (B - A)/B \times 100$$

wherein B denotes the average weight reduction rate of a not-treated wood piece, and A denotes the average weight reduction rare of a treated wood piece.

TABLES 2-1 and 2-2 show results of weatherability tests for the wood preservative compositions of EXAMPLES 1 -23. The weatherability test was carried out as follows. One wood piece treated with one of the wood preservatives of EXAMPLES 1-23 and another wood piece treated with the same preservative were prepared. The one wood piece was subjected to weathering ten times. The other wood piece was not subjected to the weathering The weathering was carried out by washing a test piece with a predetermined amount of water, and drying the washed test piece for a predetermined time.

The anti insect effectiveness of the wood preservative compositions of EXAMPLES 1-23 was determined based on tests in accordance with "GENERAL TESTS OF TESTING METHOD OF APPLYING, SPRAYING, AND IMPREGNATING WOOD PRESERVATIVES (1), LABORATORY TEST METHODS" specified in Regulation No. 11, 1981 of Japan Wood-Preservers' Association Standard, No. 12, 1981.

Specifically, a given amount of plaster was poured and solidified in a container having 8 cm in diameter and 6 cm in height. A sapwood of Japanese red pine of $2 \times 1 \times 1$ cm in size so treated was placed on the solidified plaster. 150 workers and 15 soldiers of coptotermes formosanus SHIRAKI were released in the container. Subsequently, the container was covered with a lid having air holes and wet cotton padding on the underside thereof, and held in a dark room at a temperature of 28° C. for 2 days. Thereafter, the number of dead bodies was counted, and the weight of the wood piece before and after the test were measured. TABLES 3-1 and 3-2 show results of this test. It should be noted that in TABLES 3-1 and 3-2, the upper row of each example shows data concerning the test piece not subjected to weathering, and the lower row shows data concerning the test piece subjected to weathering. Also, weatherability tests were carried out in the same way as those in the anti-fungi effectiveness test.

TABLE 1-1

| Example No. | Impregnating Amount (Kg/m³) | (Absorbed Amount) Absorbed Amount (Kg/m³) | | | | | |
|---|---|---|---|---|---|---|---|
| | | C/B | Z/B | Cu | Zn | Fixed B | Free B |
| 1 | 660 | 7.50 | — | 3.00 | — | 5.90 | — |
| 2 | 650 | 5.00 | — | 2.00 | — | 3.90 | — |
| 3 | 650 | 2.49 | 4.10 | 1.00 | 2.00 | 1.95 | — |
| 4 | 650 | 2.49 | — | 1.00 | — | 1.95 | — |
| 5 | 650 | 2.17 | — | 1.00 | — | 0.97 | 0.32 |
| 6 | 656 | 2.01 | — | 1.01 | — | 0.78 | 0.19 |
| 7 | 665 | — | 8.74 | — | 4.09 | 2.58 | 2.58 |
| 8 | 639 | — | 6.54 | — | 1.97 | 3.72 | 1.86 |
| 9 | 650 | — | 6.65 | — | 2.00 | 3.78 | 1.89 |
| 10 | 645 | 3.90 | 6.64 | 0.99 | 2.00 | 3.78 | 1.89 |
| 11 | 640 | — | 6.59 | — | 1.98 | 3.75 | 1.89 |
| 12 | 651 | — | 5.79 | — | 2.00 | 1.91 | 1.91 |
| 13 | 670 | 2.57 | 4.41 | 1.03 | 2.06 | 2.01 | 1.30 |
| 14 | 643 | 1.24 | 3.29 | 0.50 | 0.99 | 2.85 | 0.93 |
| 15 | 625 | 2.40 | 9.60 | 0.96 | 2.89 | 7.32 | 2.73 |
| 16 | 653 | 5.00 | 13.36 | 2.01 | 4.02 | 11.52 | 3.80 |
| 17 | 650 | 2.49 | 6.64 | 1.00 | 2.00 | 5.76 | 0.94 |
| 18 | 640 | 1.23 | 2.82 | 0.49 | 0.99 | 1.89 | 0.93 |
| 19 | 650 | 2.49 | 5.74 | 1.00 | 2.01 | 3.86 | 1.91 |
| 20 | 650 | 1.09 | 3.32 | 0.50 | 1.01 | 2.38 | 1.11 |
| 21 | 660 | 1.10 | 6.75 | 0.51 | 2.03 | 4.34 | 3.09 |
| 22 | 652 | 1.01 | 3.32 | 0.50 | 0.99 | 2.27 | 1.04 |
| 23 | 649 | 0.50 | 4.98 | 0.25 | 1.51 | 3.03 | 1.47 |

TABLE 1-2

| Example No. | (Leaching Rate) Leaching Rate (%) | | |
|---|---|---|---|
| | Cu | Zn | Boric Acid |
| 1 | 8.00 | — | 19.00 |
| 2 | 9.00 | — | 25.00 |
| 3 | 4.40 | 8.90 | 43.70 |
| 4 | 9.00 | — | 25.00 |
| 5 | 6.50 | — | 18.30 |
| 6 | 2.60 | — | 16.20 |
| 7 | — | 6.00 | 7.50 |
| 8 | — | 9.40 | 19.70 |
| 9 | — | 10.10 | 18.50 |
| 10 | 9.10 | 9.40 | 19.70 |
| 11 | — | 9.20 | 19.80 |
| 12 | — | 9.00 | 15.30 |
| 13 | 4.00 | 8.80 | 10.50 |
| 14 | 8.57 | 16.43 | 11.60 |
| 15 | 4.67 | 6.81 | 3.02 |
| 16 | 3.31 | 5.38 | 0.00 |
| 17 | 3.42 | 7.57 | 0.00 |
| 18 | 7.50 | 8.30 | 9.50 |
| 19 | 5.30 | 7.10 | 6.40 |
| 20 | 8.50 | 4.60 | 7.70 |
| 21 | 7.30 | 2.70 | 6.30 |
| 22 | 10.40 | 9.30 | 0.00 |
| 23 | 16.30 | 10.20 | 0.00 |

TABLE 2-1

| Example No. | (Coriolellus Palustria) | | | |
|---|---|---|---|---|
| | Average Reduction Rate of Weight (%) | | Effectiveness of Anti-Fungi (%) | |
| | No-Weather. | 10-Weather. | No-Weather. | 10-Weather. |
| 1 | 0.5 | 1.8 | 99 | 95 |
| 2 | 0.5 | 2.0 | 99 | 95 |
| 3 | 0.9 | 1.9 | 97 | 96 |
| 4 | 0.5 | 2.4 | 97 | 94 |
| 5 | 0.5 | 2.0 | 99 | 95 |
| 6 | 0.5 | 2.1 | 99 | 94 |
| 7 | 1.1 | 2.2 | 97 | 94 |
| 8 | 0.0 | 1.9 | 100 | 95 |
| 9 | 0.0 | 1.5 | 100 | 96 |
| 10 | 0.0 | 0.8 | 100 | 98 |

TABLE 2-1-continued (Coriolellus Palustria)

| Example No. | Average Reduction Rate of Weight (%) No-Weather. | Average Reduction Rate of Weight (%) 10-Weather. | Effectiveness of Anti-Fungi (%) No-Weather. | Effectiveness of Anti-Fungi (%) 10-Weather. |
|---|---|---|---|---|
| 11 | 0.0 | 1.9 | 100 | 95 |
| 12 | 1.0 | 2.5 | 97 | 93 |
| 13 | 0.0 | 1.1 | 100 | 97 |
| 14 | 0.4 | 1.9 | 99 | 95 |
| 15 | 0.0 | 0.3 | 100 | 99 |
| 16 | 0.0 | 0.0 | 100 | 100 |
| 17 | 0.0 | 0.8 | 100 | 98 |
| 18 | 0.2 | 0.7 | 99 | 98 |
| 19 | 0.0 | 1.0 | 100 | 97 |
| 20 | 0.2 | 0.8 | 99 | 98 |
| 21 | 0.0 | 0.6 | 100 | 98 |
| 22 | 0.2 | 0.8 | 99 | 98 |
| 23 | 0.3 | 0.7 | 99 | 98 |
| Not treated | 37.3 | | | |

TABLE 2-2

(Coriolus Versicolor)

| Example No. | Average Reduction Rate of Weight (%) No-Weather. | Average Reduction Rate of Weight (%) 10-Weather. | Effectiveness of Anti-Fungi (%) No-Weather. | Effectiveness of Anti-Fungi (%) 10-Weather. |
|---|---|---|---|---|
| 1 | 0.4 | 1.0 | 98 | 96 |
| 2 | 0.9 | 1.8 | 96 | 92 |
| 3 | 0.8 | 1.6 | 97 | 94 |
| 4 | 1.2 | 2.5 | 95 | 89 |
| 5 | 1.0 | 2.5 | 96 | 89 |
| 6 | 1.1 | 2.7 | 95 | 89 |
| 7 | 1.2 | 1.9 | 95 | 92 |
| 8 | 0.5 | 1.4 | 98 | 94 |
| 9 | 0.5 | 1.7 | 98 | 93 |
| 10 | 0.5 | 1.4 | 98 | 94 |
| 11 | 0.5 | 2.0 | 98 | 91 |
| 12 | 1.3 | 2.3 | 94 | 90 |
| 13 | 0.5 | 1.4 | 98 | 94 |
| 14 | 0.9 | 1.4 | 96 | 94 |
| 15 | 0.5 | 1.3 | 98 | 94 |
| 16 | 0.5 | 1.2 | 98 | 95 |
| 17 | 0.5 | 1.3 | 98 | 94 |
| 18 | 0.7 | 1.5 | 97 | 94 |
| 19 | 0.3 | 1.5 | 99 | 95 |
| 20 | 0.7 | 1.5 | 97 | 94 |
| 21 | 0.5 | 1.1 | 98 | 95 |
| 22 | 0.8 | 1.3 | 97 | 94 |
| 23 | 1.0 | 2.2 | 96 | 91 |
| Not-treated | 23.5 | | | |

TABLE 3-1

| Example No. | Death Rate (%) Min.-Max. | Death Rate (%) Average | Reduction Rate of Weight (%) Min.-Max. | Reduction Rate of Weight (%) Average |
|---|---|---|---|---|
| 1 | 100–100 | 100 | 0.13–0.75 | 0.40 |
|   | 98–100 | 99 | 0.21–0.96 | 0.61 |
| 2 | 100–100 | 100 | 0.20–0.80 | 0.52 |
|   | 95–100 | 98 | 0.32–1.00 | 0.65 |
| 3 | 100–100 | 100 | 0.21–0.78 | 0.50 |
|   | 95–100 | 97 | 0.35–0.99 | 0.60 |
| 4 | 100–100 | 100 | 0.15–0.75 | 0.50 |
|   | 97–100 | 97 | 0.30–0.90 | 0.60 |
| 5 | 100–100 | 100 | 0.20–0.75 | 0.50 |
|   | 95–100 | 98 | 0.30–0.90 | 0.60 |
| 6 | 100–100 | 100 | 0.30–1.10 | 0.70 |
|   | 93–100 | 97 | 0.40–1.50 | 1.00 |
| 7 | 100–100 | 100 | 0.00–0.20 | 0.10 |
|   | 97–99 | 98 | 0.20–0.50 | 0.40 |
| 8 | 100–100 | 100 | 0.00–0.20 | 0.10 |
|   | 100–100 | 100 | 0.00–0.30 | 0.20 |
| 9 | 100–100 | 100 | 0.00–0.15 | 0.10 |
|   | 100–100 | 100 | 0.00–0.15 | 0.10 |
| 10 | 100–100 | 100 | 0.00–0.15 | 0.10 |
|   | 100–100 | 100 | 0.00–0.15 | 0.10 |
| 11 | 100–100 | 100 | 0.00–0.20 | 0.10 |
|   | 97–100 | 99 | 0.20–0.75 | 0.48 |
| 12 | 100–100 | 100 | 0.20–0.80 | 0.52 |
|   | 95–100 | 98 | 0.30–1.00 | 0.65 |

TABLE 3-2

| Example No. | Death Rate (%) Min.-Max. | Death Rate (%) Average | Reduction Rate of Weight (%) Min.-Max. | Reduction Rate of Weight (%) Average |
|---|---|---|---|---|
| 13 | 100–100 | 100 | 0.00–0.20 | 0.10 |
|   | 98–100 | 99 | 0.00–0.30 | 0.21 |
| 14 | 100–100 | 100 | 0.20–0.75 | 0.50 |
|   | 95–100 | 98 | 0.30–0.90 | 0.60 |
| 15 | 100–100 | 100 | 0.00–0.20 | 0.10 |
|   | 97–99 | 98 | 0.20–0.50 | 0.40 |
| 16 | 100–100 | 100 | 0.00–0.00 | 0.00 |
|   | 100–100 | 100 | 0.00–0.00 | 0.00 |
| 17 | 100–100 | 100 | 0.25–0.75 | 0.50 |
|   | 96–100 | 98 | 0.40–0.90 | 0.65 |
| 18 | 100–100 | 100 | 0.20–0.80 | 0.50 |
|   | 94–100 | 97 | 0.40–0.90 | 0.65 |
| 19 | 100–100 | 100 | 0.25–0.75 | 0.50 |
|   | 95–100 | 97 | 0.45–0.97 | 0.71 |
| 20 | 100–100 | 100 | 0.20–0.75 | 0.50 |
|   | 95–100 | 98 | 0.30–0.90 | 0.60 |
| 21 | 100–100 | 100 | 0.20–0.70 | 0.45 |
|   | 95–100 | 98 | 0.40–0.80 | 0.60 |
| 22 | 100–100 | 100 | 0.20–0.75 | 0.50 |
|   | 95–100 | 98 | 0.30–0.90 | 0.60 |
| 23 | 100–100 | 100 | 0.10–0.50 | 0.30 |
|   | 96–100 | 98 | 0.20–0.75 | 0.50 |

What is claimed is:

1. A wood preservative composition comprising:
   a preservative component selected from the group consisting of copper tetraborate monobasic, copper tetraborate dibasic, zinc tetrahydroxide tri (tetraboric acid) salt, zinc hydroxide dimetaboric acid salt, and mixtures thereof, the content by weight of said preservative component with respect to 100 parts by weight of the wood preservative composition being 0.1–10.0 parts;
   a volatile basic compound of the formula $R_3N$, wherein R is selected from the group consisting of a hydrogen atom and a lower alkyl group, the content by weight of said volatile basic compound with respect to 100 parts by weight of the preservative component being 75–160 parts; and
   water.

2. A wood preservative composition according to claim 1, wherein said preservative component is selected from the group consisting of copper tetraborate monobasic, copper tetraborate dibasic and copper tetraborate tribasic, the content by weight of said preservative component with respect to 100 parts by weight of the wood preservative composition being 0.1–10.0 parts; and
   wherein the content by weight of said volatile basic compound with respect to 100 parts by weight of said preservative component is 80–160 parts.

3. A wood preservative composition according to claim 2, wherein the content of said preservative component is 0.5–2.0 parts.

4. A wood preservative composition according to claim 2 wherein the content of said volatile basic compound is 80–100 parts.

5. A wood preservative composition according to claim 1, wherein said preservative component is selected from the group consisting of zinc tetraborate dibasic, zinc tetrahydroxide tri(tetraboric acid) salt and zinc hydroxide dimetaboric acid salt, the content by weight of said preservative component with respect to 100 parts by weight of the wood preservative composition being 0.1–10.0 parts; and
   wherein the content by weight of said volatile basic compound with respect to 100 parts by weight of said preservative component is 75–160 parts.

6. A wood preservative composition according to claim 5, wherein the content of said preservative component is 0.5–2.0 parts.

7. A wood preservative composition according to claim 5, wherein the content of said volatile basic compound is 75–100 parts.

8. A wood preservative composition according to claim 2, further comprising an additional preservative component comprising a zinc compound other than zinc tetraborate dibasic, zinc tetrahydroxide tri(tetraboric acid) salt and zinc hydroxide dimetaboric acid salt.

9. A wood preservative composition according to claim 5, further comprising an additional preservative component comprising a copper compound other than copper tetraborate monobasic, copper tetraborate dibasic and copper tetraborate tribasic.

10. A wood preservative composition according to claim 1, wherein said volatile basic compound is an amine.

11. A wood preservative composition according to claim 1, wherein said volatile basic compound is ammonia.

12. A wood preservative composition comprising:
   a preservative component comprising a mixture of (A) and (B) wherein (A) is selected from the group consisting of copper tetraborate monobasic, copper tetraborate dibasic, copper tetraborate tribasic, and mixtures thereof, and (B) is selected from the group consisting of zinc tetraborate dibasic, zinc tetrahydroxide tri (tetraboric acid) salt, zinc hydroxide dimetaboric acid salt, and mixtures thereof, the content by weight of said preservative component with respect to 100 parts by weight of the wood preservative composition being 0.1 to 10.0 parts;
   a volatile basic compound of the formula $R_3N$, wherein R is selected from the group consisting of a hydrogen atom and a lower alkyl group, the content by weight of said volatile basic compound with respect to 100 parts by weight of the preservative component being 75–160 parts; and
   water.

* * * * *